United States Patent
Triche et al.

(10) Patent No.: US 7,939,335 B1
(45) Date of Patent: May 10, 2011

(54) DETECTION AND CLASSIFICATION OF HEAVY HYDROCARBON CONTAMINATION IN REFINERY PROCESS STREAMS VIA SPECTROFLUOROMETRY

(75) Inventors: Nicole R. Triche, Canton, OH (US); Axel J. Lubeck, Littleton, CO (US)

(73) Assignee: Marathon Ashland Petroleum LLC, Findlay, OH (US)

( * ) Notice: Subject to any disclaimer, the term of this patent is extended or adjusted under 35 U.S.C. 154(b) by 175 days.

(21) Appl. No.: 12/291,075

(22) Filed: Nov. 6, 2008

Related U.S. Application Data

(62) Division of application No. 10/942,489, filed on Sep. 16, 2004, now Pat. No. 7,501,285.

(51) Int. Cl.
*G01N 33/00* (2006.01)

(52) U.S. Cl. .................. 436/139; 436/172; 422/82.08

(58) Field of Classification Search .............. 436/139, 436/172; 422/82.06
See application file for complete search history.

(56) References Cited

U.S. PATENT DOCUMENTS

| | | | |
|---|---|---|---|
| 5,111,882 A | 5/1992 | Tang et al. |
| 5,246,860 A | 9/1993 | Hutchins et al. |
| 6,271,518 B1 | 8/2001 | Boehm et al. |
| 6,331,436 B1 | 12/2001 | Richardson et al. |
| 6,420,181 B1 | 7/2002 | Novak |

*Primary Examiner* — Sam P Siefke
(74) *Attorney, Agent, or Firm* — Emch, Schaffer, Schaub & Porcello, Co., L.P.A.

(57) ABSTRACT

A method and apparatus for determining the presence of heavy hydrocarbons (including those from unprocessed crude oil) in distillate streams and/or reformer feed includes taking at least one sample, spectrally analyzing the at least one sample for at least one heavy hydrocarbon component, determining the concentration of the analyzed hydrocarbon component using the spectrally determined concentration in an appropriate mathematical model, and determining the total heavy hydrocarbon concentration from the determined values for each sample.

4 Claims, 2 Drawing Sheets

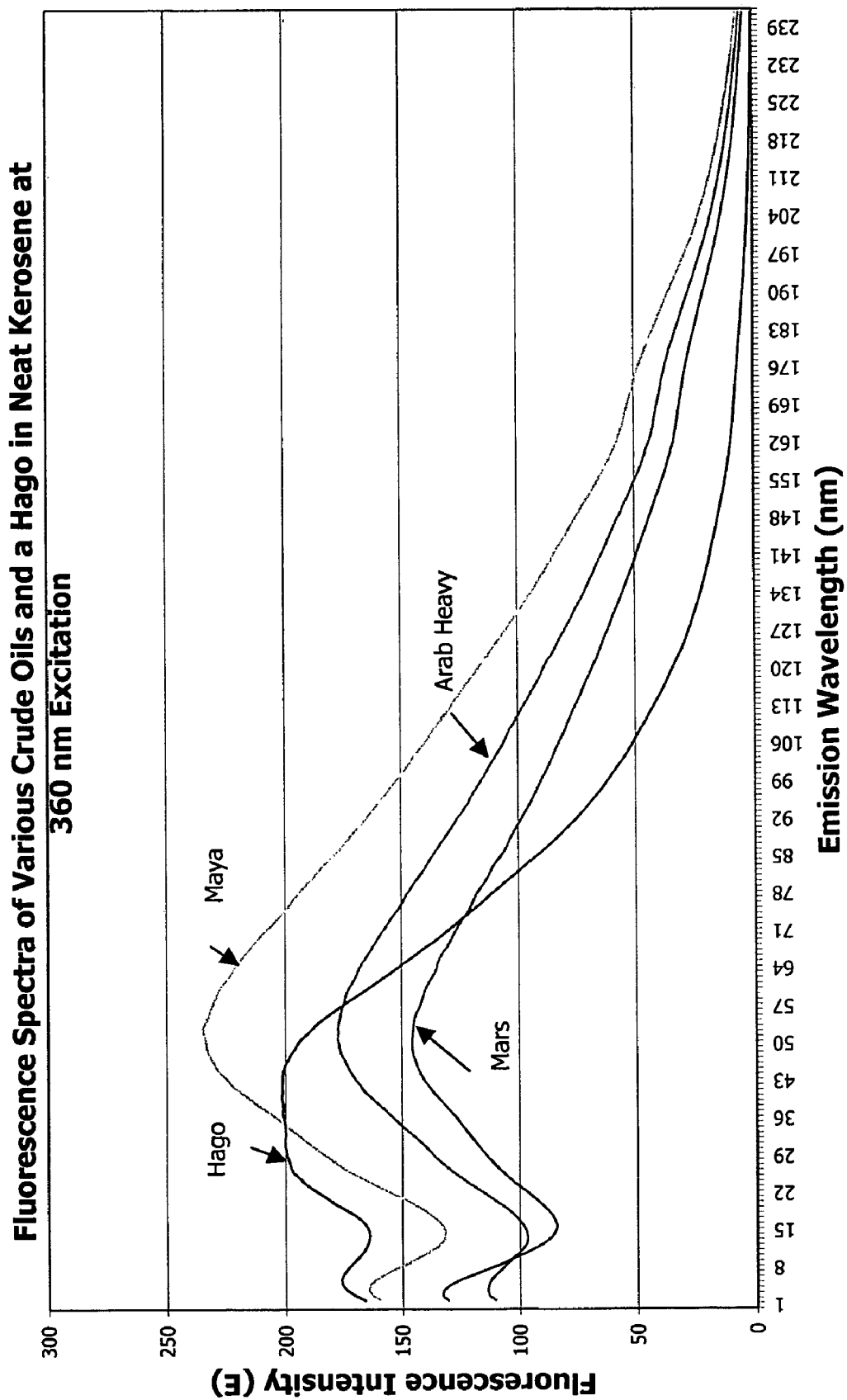

DETECTION AND CLASSIFICATION OF HEAVY HYDROCARBON CONTAMINATION IN REFINERY PROCESS STREAMS VIA SPECTROFLUOROMETRY

CROSS REFERENCE TO RELATED APPLICATION

This application is a divisional of and claims the benefit of U.S. patent application Ser. No. 10/942,489 filed Sep. 16, 2004 now U.S. Pat. No. 7,501,285.

BACKGROUND OF THE INVENTION

I. Field of the Invention

The present invention relates to a method for the detection and classification by type of heavy hydrocarbon contaminants in petroleum refinery process streams using spectrofluorometry.

II. Description of the Prior Art

There are numerous, industry-accepted test methods for the analysis of physical and chemical properties of hydrocarbons which, alone or in combination, have been used to detect the presence of hydrocarbon contaminants in various refinery process streams and/or to classify them as to type. These methods have been approved by organizations such as ASTM (American Society for Testing Materials), IP (Institute of Petroleum, United Kingdom), and DIN (Deutsches Institut fur Normung, Germany), as well as private companies which provide analytical instrumentation or which license processes to refineries. These would include methods such as: ASTM D-86 distillation temperatures at various percentages distilled; ASTM D-1298 test for API gravity; Gas chromatography—Mass spectrometry (GC Mass Spec) for determination of weight percent aromatics; and ASTM D-2622 for sulfur, ASTM D3710-95 Boiling Range Distribution of Gasoline and Gasoline Fractions; ASTM D2789-25 Hydrocarbon Types in Low Olefinic Gasoline by Mass Spectrometry; ASTM D4534 Benzene Content of Cyclic Products; ASTM D5134-92 Detailed Analysis of Petroleum Naphtha through n-Nonane by Capillary GC; ASTM D5443-93 Paraffin, Naphthene and Aromatic Hydrocarbon Type Analysis in Petroleum Distillates; ASTM D5769-95 Determination of Benzene, Toluene and Total Aromatics in Finished Gasoline by GC/MS; ASTM D6293-99 Oxygenates and Paraffin, Olefin, Naphthene, Aromatic (O-PONA) Hydrocarbon Types in Low-Olefin Spark-Ignition Engine Fuels by Gas Chromatography; ASTM D6296-98 Total Olefins in Spark-Ignition Engine Fuels by Multi-dimensional Gas Chromatography; IP 382/88 Paraffin, Naphthene and Aromatic Hydrocarbon Type Analysis in Petroleum Distillates; IP BG/91 (proposed) Determination of methyl tertiarybutyl ether and tertiaryamyl methyl ether in Light Distillate Feedstock; DIN, 51.448, part 2 Paraffin, Naphthene and Aromatic Hydrocarbon Type Analysis in Petroleum Distillates; DIN Method, 51.448 part 2, Oxygenates and Paraffin, Olefin, Naphthene, Aromatic (O-PONA) Hydrocarbon Types; UOP 870 Paraffin, Naphthene and Aromatic Hydrocarbon Type Analysis in Petroleum Distillates; High Speed Simulated Distillation of Light Hydrocarbons, Gasoline and Gasoline Feedstocks; Detailed Hydrocarbon Analysis (DHA) of Non-Oxygenated Gasoline and Hydrocarbon Liquids using stream dedicated databases; High Speed Detailed Hydrocarbon Analysis of Non-Oxygenated Gasoline and Hydrocarbon Liquid; Individual Hydrocarbon Analysis of Gasolines and Light Fractions (PIANO/IHA/DHA) by Gas Chromatography; High Speed Detailed Hydrocarbon Analysis of Non-Oxygenated Gasoline and Hydrocarbon Liquids; DHA of Oxygenated Gasoline and Gasoline Feedstocks; Simultaneous Nitrogen and Hydrocarbon Analysis by GC with Flame Ionization and Chemiluminescence Detection in Light Petroleum Liquids; Sulfur Compounds in Distillates by GC-Chemiluminescence Detection; Sulfur Distribution in Petroleum Distillates by Simultaneous HPLC-UV and Chemiluminescence Detection; Nitrogen, Sulfur and Carbon Distribution in Distillates by GC-Chemiluminescence and Flame Ionization detection; Multi-Elemental Boiling Point Distribution Analysis Using the Atomic Emission Detector (AED) on Petrochemical Samples with a Final Boiling Point Below 650° F.; Sulfur and Carbon Distribution in Light Petroleum Products by Simultaneous GC-FID and GC-Sulfur Specific Detection; Low level S analysis -ppm to sub-ppb; Analysis of Paraffins in Kerosene (C5-C20) by Subtractive Gas Chromatography; PIANO analysis of gasoline and gasoline boiling-range blending streams, automatic peak ID and reporting; High Speed Contaminant Analysis Using Mass Spectrometry with Matrix Deconvolution; Aromatic and Saturate Types in Petroleum Distillates.

Conventionally, these tests are conducted using many different types of apparatuses. These tests are time-consuming and relatively expensive. These tests also lack sensitivity to detect contaminants at low concentrations and lack specificity to determine the type of contaminant. The contamination of light refinery process streams with heavy aromatics is an ongoing concern in the petroleum industry. Such contamination can cause severe processing problems and/or result in final products which do not meet contractual or government specifications. To mitigate and control this problem in particular, it is desired to detect the presence and type of the heavy aromatics and to identify its source. Often, the source of contamination is one or more heat exchanger leaks occurring in the system.

Detection and classification is complicated by the fact that there are both gas oil exchangers and crude oil exchangers and the materials in these exchangers both fluoresce in the same wavelength range. It is to be noted that exchanger leaks on the crude units typically occur on two-year cycles due to the age of the exchangers (basically, once the exchangers begin leaking, the exchangers are replaced). It is, therefore, important to find the correct exchanger, which can be difficult (especially if more that one is leaking). Past exchanger leak episodes and their detection have been marginally successful. Often detection of the exchanger leak was more due to operator knowledge than successful use of other methods. The instruments being used could only detect that there were heavy aromatics in the stream; however, there was no identification of the types of heavy aromatics that were present.

It is desired, therefore, to have an on-line testing apparatus installed on or "at" a feedstock stream to monitor the degree of contamination and the type of contaminant.

SUMMARY OF THE INVENTION

This invention relates to the detection of heavy hydrocarbon substances and measurement of the quantities of such heavy hydrocarbon substances present. In certain embodiments, the method detects heavy aromatic hydrocarbons in naphtha and certain types of distillate streams such as kerosene.

In certain embodiments, the present invention is especially useful for detecting heavy hydrocarbons (including those from unprocessed crude oil) in reformer feed.

More particularly, the present invention relates to qualitative and quantitative analysis utilizing spectrofluorometry of the substances under analysis.

In one aspect, the present invention relates to a method for measuring any differences in the peak location (wavelength of maximum fluorescence) and shape (profile of fluorescence spectrum) by using spectrofluorometry to compare crude oil contamination to gas oil contamination. The ability to differentiate between crude oil and gas oil peaks greatly aids in narrowing down the search field for the exchanger leak(s).

It is an object of this invention to provide methods and apparatuses for qualitative and quantitative analysis of heavy aromatic contaminants in reformer feed and for crude unit exchanger leak detection utilizing spectrofluorometry. More specifically, it is an object of this invention to provide the capability of performing analyses rapidly and through a relatively unskilled technician or without a technician in attendance at all.

It is also an object of the present invention to provide methods and apparatus where little or no human judgment and/or human interpretation are necessary to produce analytical results.

It is also an object of this invention to provide methods and apparatus for rapidly analyzing substances which have heretofore required complex procedures involving much sample handling and/or pretreatment by various procedures.

Also, it is an object of this invention to provide an analysis which requires only a small amount of sample and to provide a non-destructive method of analysis such that the sample is not altered or consumed. This object is related to that of providing apparatus which consumes little electrical power and does not heat the sample.

It is a further object of this invention to provide a method and apparatus to analyze a substance in situ, that is, without withdrawing the substance from a containing vessel or pipeline.

It is a still further object of this invention to provide an analysis apparatus which is modular in design and construction, to facilitate troubleshooting and repair.

Another object of this invention is to provide a universal method and apparatus instead of such capable of use in analyzing only certain substances or use in only particular specialized applications. It is also desired to provide apparatus which is inexpensive in relation to its utility.

Other objects and advantages of the present invention will become apparent to those skilled in the art upon a review of the following detailed description of the preferred embodiments and the accompanying drawings.

DESCRIPTION OF THE FIGURES

FIG. 2 is a graph showing fluorescence intensity versus emission wavelength for a gas oil in kerosene sample and a crude oil in kerosene sample in comparison to off-specification kerosene contaminated with unknown heavy aromatic.

DESCRIPTION OF THE PREFERRED EMBODIMENTS

Figure 1:
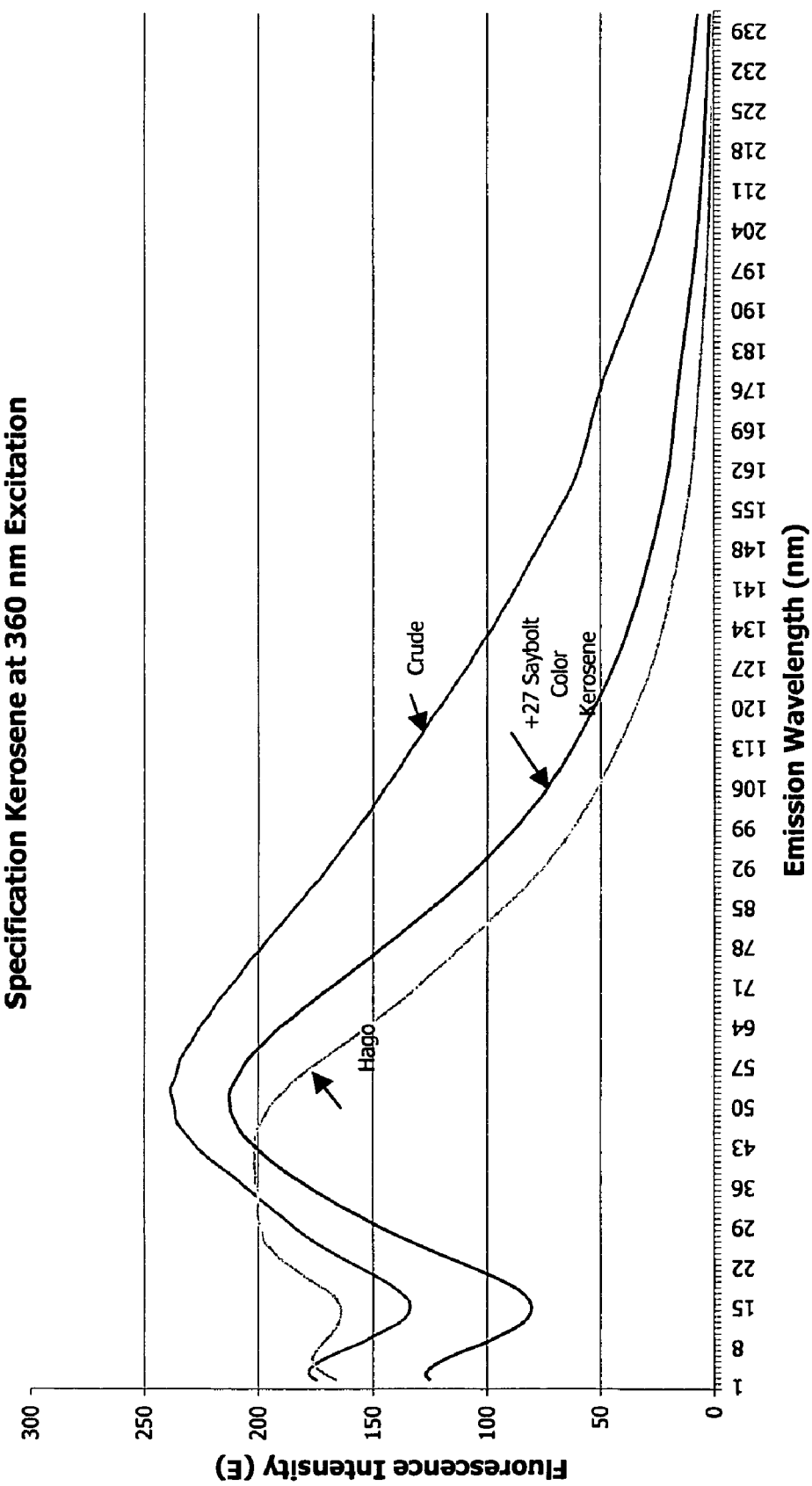
FIG. 1 is a graph showing fluorescence intensity versus emission wavelength for various types of crude oils (Maya, Mars; Arab Heavy) vs. Hago (heavy atmospheric gas oil) added as contaminants to neat kerosene (kero).

The present invention relates to a method to detect heavy hydrocarbon contamination in reformer feed (naphtha) using an analytical technique known as spectrofluorometry.

The present invention provides improvements in the detection, identification and classification of heavy hydrocarbon components.

The method of the invention overcomes the difficulties with the earlier detection methods, in particular avoiding all difficulties with the rapid and accurate identification of where any leak is occurring in the system. The method of the present invention thus allows easy and rapid identification and classification of a sample analyzed by fluorospectral recognition and then instant conclusions as to whether the sample is known or unknown, allowing simultaneous determination of many properties of the sample.

"Heavy hydrocarbons" are generally defined as viscous hydrocarbon fluids. Heavy hydrocarbons may include highly viscous hydrocarbon fluids such as heavy oil, tar, and/or asphalt. Elements in heavy hydrocarbons may include carbon and hydrogen, as well as smaller concentrations of sulfur, oxygen, and nitrogen. Additional elements may also be present in heavy hydrocarbons in trace amounts. Heavy hydrocarbons may be classified by API gravity. Heavy hydrocarbons generally have an API gravity below about 20°. Heavy oil, for example, generally has an API gravity of about 10-20° whereas tar generally has an API gravity below about 10°. The viscosity of heavy hydrocarbons is generally greater than about 300 centipoise at 15° C. Tar generally has a viscosity greater than about 10,000 centipoise at 15° C. Heavy hydrocarbons may also include aromatics, or other complex ring hydrocarbons, including, for example, heavy hydrocarbons such as diesel fuel, fuel oil, or crude oil. Heavy hydrocarbons may be found in a relatively permeable formation. The relatively permeable formation may include heavy hydrocarbons entrained in, for example, sand or carbonate. "Relatively permeable" is defined, with respect to formations or portions thereof, as an average permeability of 10 millidarcy or more (e.g., 10 or 100 millidarcy). "Relatively low permeability" is defined, with respect to formations or portions thereof, as an average permeability of less than about 10 millidarcy. One Darcy is equal to about 0.99 square micrometers. An impermeable layer generally has a permeability of less than about 0.1 millidarcy.

"Spectrofluorometry" is a method of chemical analysis in which a sample, exposed to light at one wavelength (excitation), absorbs this radiation and re-emits light at another, longer wavelength (emission). The intensity of the emission is proportional to the concentration of the fluorescing species. For samples containing more than one fluorescing species, the excitation and emission occurs not at a single wavelength but over a range of wavelengths.

Luminescence occurs when a material is activated by an energy stimulus whereby the molecules are raised to an excited state. When the stimulus ends, these molecules drop back to a less excited state and give off light energy while doing so. Herein, "light" is defined to be substantially the entire electromagnetic spectrum where excitation and luminescence can be found. If the emitted light energy lasts for a short time, the effect is referred to as "fluorescence" and as "phosphorescence when the emitted energy lasts for a longer duration. In practice these terms are often used interchangeably.

Spectrofluorometers or fluorometers, use a narrow band (e.g., 0.5 to 10 nanometers) of UV (ultraviolet) light as an excitation source. The emitted light of a luminescing sample will always be of longer wavelength than the wavelength of the source excitation. This is because lower energy corresponds to longer wavelengths, and due to the law of conservation of energy the emitted light's energy cannot exceed the excitation light's energy. The emitted light will not be of equal wavelength to the excitation light's wavelength (resonance fluorescence), since some of the energy in the system is lost due to molecular collisions and to thermal dissipation. Therefore the emitted light will be of lower energy and hence longer wavelength. The emitted light is selectively filtered according to wavelength, and, then, the intensity of one or more wavelengths is measured via a photodetector.

The sample of material excited with light of a particular wavelength emits light energy in the form of an emission spectrum whose amplitude profile, over the range of wavelengths emitted, constitutes a "fingerprint" which gives the identity and nature of the unknown material in the sample. The result is a highly accurate, so-called three-dimensional fluorescence emission spectrum, showing excitation wavelengths, corresponding emission wavelengths and their amplitudes.

The method of the present invention provides information on subtle variations in the characteristics of the sample and also provides useful information on relatively subtle changes in the system. The optimum excitation and emission wavelengths generally increase with molecular size (number of benzene rings in the molecule) of the aromatics. Most aromatic hydrocarbons are strongly fluorescing species such that the spectrofluorometric method of the present invention provides a very sensitive method for detecting heavy hydrocarbon contamination in reformer feed (naphtha).

The method of the present invention compares the characteristics of aromatic hydrocarbons present in the streams (i.e., the streams contain aromatics of different molecular size) using fluorescence to provide a measurable detection of any contamination of one crude unit stream with another.

For example, in a virgin naphtha, the aromatics are predominantly mononuclear (containing only a single benzene ring in the molecule). In contrast, virgin diesel has a predominance of 2-ring aromatics (naphthalenes) with some 3-ring structures (although, severely hydrotreated diesels may be mostly mononuclear). Gas oils consist mostly of 3-ring or larger aromatics. The method of the present invention thus measures the differences in the aromatics among these streams to detect traces of heavy hydrocarbons.

According to one aspect of the present invention, by proper selection of excitation and emission wavelengths, the emission signal from the naphtha aromatics is minimized and the emission signal from the contaminant stream aromatics is maximized. To enhance this selection process a spectrofluorometer with the capability to provide a continuous scan of fluorescence intensity over a selected range of emission wavelengths is used. It is to be understood that the precise wavelength being measured depends, at least in part, on the material being sampled. For example, in certain embodiments, fluorescence is measured at about 320 nm to detect diesel-type (2-3 ring aromatics) contamination and is measured at about 360 nm to detect crude oil and/or gas oil-type (heavier aromatics) contamination. Accordingly, one aspect of the present invention provides methods for (i) the determination and/or control of heavy aromatics in reformer feed and (ii) for the detection of heavy aromatics in distillate streams.

In another embodiment, the present invention provides a method for determining the presence of heavy hydrocarbons in distillate streams and/or reformer feed comprising:
    taking multiple samples,
    spectrally analyzing each of the samples for at least one heavy hydrocarbon aromatic component,
    determining the concentration of the analyzed component using the spectrally determined concentration in an appropriate mathematical model, and
    determining the total heavy hydrocarbon concentration from the determined values for each sample.

In one of its embodiments, the invention comprises a method for performing a quantitative analysis for heavy aromatic substances in naphtha and distillate samples. The method of the present invention includes:
    (a) using a spectrofluorometer to producing a beam of photons which is substantially monochromatic and impinges on the unknown sample;
    (b) collecting photons emitted by the unknown sample into a stream of emitted photons;
    (c) resolving the photon stream into its component frequencies to form a spectrum of the unknown sample;
    (d) converting the unknown sample spectrum to digital form and transmitting the unknown spectrum to computing means;
    (e) comparing reference spectra obtained in the same manner as the unknown spectrum, where the reference spectra are of reference samples whose quantitative composition is known and where each reference sample is comprised of at least one of the preselected substances; and,
    (f) identifying substances present in the unknown sample by comparing said unknown spectrum to the reference spectra.

It is also within the contemplated scope of the present invention that the comparison be accomplished by using a method comprising the following steps:
    (i) inspecting the reference spectra and selecting a plurality of separate spectral analysis regions;
    (ii) determining the areas of the selected regions for each reference spectrum and for the unknown spectrum;
    (iii) establishing a relationship between the reference spectra region areas and concentrations of the preselected substances in the reference samples; and
    (iv) determining the concentrations of the preselected substances in the unknown sample by applying the relationship established in step (iii) to the unknown spectrum region areas.

The above described relationship may be established and the concentrations determined by:
    (a) expressing the reference sample concentrations in terms of concentration fractions and arranging the concentration fractions in a concentration fraction matrix, according to the reference samples and the preselected substances;
    (b) calculating area fractions from the reference spectra region areas and arranging the area fractions into an area fraction matrix, according to the reference samples and the selected regions;
    (c) forming a suitable mathematical relationship;
    (d) solving a mathematical quantity to yield a matrix, which comprises at least one or more correlation coefficients, arranged according to the selected regions and the preselected substances.

It is to be understood that composite reference spectra may be used in performing the comparison. The composite reference spectrum can be prepared for each reference sample by providing a plurality of spectra of each reference sample to the computer and averaging each of said plurality of reference spectra.

Examples

Spectra of fluorescence intensity versus emission wavelength for various types of crude oils (Maya, Mars, Arab Heavy) and Hago (heavy atmospheric gas oil) in neat kerosene (kero) were obtained, as shown in FIG. 1

Spectra of fluorescence intensity versus emission wavelength for a gas oil and a crude oil in kerosene were obtained and compared to off-specification kerosene, as shown in FIG. 2.

Accordingly, the invention, in another embodiment, relates to a process for determining the concentration and changes in concentrations over time of one or more heavy hydrocarbons in a specified sample using spectrofluorometry. The spectrofluorometric data from the sample is collected, transferred, and transformed into data corresponding to the chemical composition of the components of the sample and concentration of said components. The concentrations of one or more heavy hydrocarbons present are then determined by processing the data from the sample according to predetermined models. As those skilled in the art will be aware, a sample may be static or dynamic, i.e., may vary over time. The terms "sample" or "samples", in this context, include flowing (or dynamic) streams of such mixtures, which are particularly preferred for real-time measurement and/or control of processes in response to frequent analysis according to the invention.

Temporal discrimination of such dynamic streams requires that data be acquired during a finite time interval. The shorter the interval, the higher temporal resolution of the changing concentration. Thus, data may be acquired over a very short time (seconds), or over a longer time (minutes). Again, only selected portions of the data obtained need be processed, as will be evident to those skilled in the art; it is to be noted that language herein indicating processing of data is to be understood to indicate processing of all or of selected data. The speed of analysis obtainable by the present invention (in certain embodiments, less than one minute) enables on-line measurement and/or control response times not possible with past prior art methods.

According to the present invention, the determination of different components may be made simultaneously and nearly continuously, providing on-line (or at-line) analysis without the need to return samples to control laboratories in refineries.

The invention thus provides a quick and efficient method of monitoring the presence and/or concentration of heavy hydrocarbons, and the monitoring system may be coupled, in the most preferred aspects of the invention, with a computer and other equipment to regulate the parameters of a process.

Thus, in another aspect, the method comprises steps of:
measuring fluorescence and producing fluorescence signals (or mathematical functions, for example, by using derivatives thereof) by the spectrofluorometer in accordance therewith;
accessing the databanks of the computer in accordance with the fluorescence signals (or functions thereof); and,
comparing, by the computer, the fluorescence signals (or functions thereof) to the signals (or functions thereof) of the standards for heavy hydrocarbon components stored in the databanks; and, in certain embodiments, optionally
controlling the process by, for example, stopping the process or taking other appropriate action to remove the heavy hydrocarbons.

The present invention also provides an apparatus suitable for carrying out the method of the invention comprising at least one spectrofluorometer and at least one computer. The spectrofluorometer is linked to the computer in such manner that the detection of any heavy hydrocarbon components may be determined continuously and in real time to determine the nearest standard. The computer is linked to at least one suitable control means to provide a suitable signal as to the presence and/or the identity of the heavy hydrocarbon components. The computer is also linked to a suitable means to control, adjust and/or stop the process when certain predetermined standards are not met.

The spectrofluorometer receives at least one signal from a vessel containing the material to be tested from a feed or product line. The spectrofluorometer is suitable for measuring fluorescence and can be linked to a signal processing device to allow numerical treatment of the spectrum. The information obtained can be used as an information vector for the computer which is programmed to determine the presence and identity of any heavy hydrocarbon components and/or determine desired standards; e.g., via calculations on proximity indices in relation to standards.

The computer may be used in a closed loop feed back or feed forward control system for controlling processing equipment; e.g., changing the process parameters in response to variations from a desired value for the presence/absence and/or identity of the heavy hydrocarbon components.

It is also within the contemplated scope of the present invention that the computer includes databanks having stored therein signals indicative of fluorescence spectra of standards for heavy hydrocarbon components (or mathematical functions thereof) and corresponding properties of said heavy hydrocarbon components.

It is also within the contemplated scope of the present invention that the method for qualitatively and quantitatively measuring the presence of heavy hydrocarbons further include the use an output signal which is transmitted to optimizing software which then continuously analyzes the signals, and downloads the updated data to be reported or to sound an alarm, if necessary.

Modifications

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein. For example, while the invention has been illustrated with monitoring reformer feed to minimize coking and for detecting crude unit exchanger leak, the invention is applicable to detecting heavy hydrocarbons in various types of distillate streams.

Reference to documents made in the specification is intended to result in such patents or literature being expressly incorporated herein by reference including any patents or other literature references cited within such documents.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. A method for the detection of heavy hydrocarbon components in at least one sample taken from a distillate stream or reformer feed comprising:
a) measuring the fluorescence of the at least one sample, or of at least one heavy hydrocarbon component of the sample, using spectrofluorometry in at least one band of the electromagnetic spectrum for determining a concentration of heavy hydrocarbon component for the at least one heavy hydrocarbon component;
b) transforming the fluorescence measured in step a) by mathematical transformation to obtain a mathematically transformed fluorescence value with a computer configured for determining the concentration of the analyzed hydrocarbon component using the spectrally determined concentration in an appropriate mathematical model;

c) periodically or continuously outputting a periodic or continuous signal indicative of the intensity of the fluorescence in the band or at least one mathematical function or a combination of mathematical functions thereof with the computer wherein the computer is configured for determining the total heavy hydrocarbon concentration from the determined values for each sample;

d) mathematically converting the signal to an output signal indicative of at least on of the presence and identification of heavy hydrocarbon components with the computer; and e) using the spectrofluorometry and the computer in such manner that the detection of any heavy hydrocarbon component is determined continuously and in real time.

2. The process of claim 1, in which the at least portion of the sample flows substantially intermittently or continuously past a point where the measurement is being made.

3. The process of claim 1, in which the fluorescence of heavy hydrocarbons is in the range of about 320 to about 360 nm.

4. An apparatus for the detection of heavy hydrocarbon components in at least one sample taken from a distillate stream or reformer feed comprising:

a) at least one means using a spectrofluorometer for measuring the fluorescence of the at least one sample, or of at least one heavy hydrocarbon component of the sample, using spectrofluorometry in at least one band of the electromagnetic spectrum for determining a concentration of heavy hydrocarbon component for the at least one heavy hydrocarbon component;

b) at least one means using a computer for transforming the fluorescence measured in step a) by mathematical transformation to obtain a mathematically transformed fluorescence value wherein the computer is configured for determining the concentration of the measured hydrocarbon component using the spectrally determined concentration in an appropriate mathematical model;

c) at least one means using the computer for periodically or continuously outputting a periodic or continuous signal indicative of the intensity of the fluorescence in the band or at least one mathematical function or a combination of mathematical functions thereof wherein the computer is configured for determining the total heavy hydrocarbon concentration from the determined values for each sample;

d) at least one means using the computer for mathematically converting the signal to an output signal indicative of at least on of the presence and identification of heavy hydrocarbon components; and e) a first link connecting the spectrofluorometer and the computer in such manner that the detection of any heavy hydrocarbon components is determined continuously and in real time.

* * * * *